United States Patent [19]
Goddard, III et al.

[11] Patent Number: 5,939,503
[45] Date of Patent: Aug. 17, 1999

[54] GROUP IV ZWITTERION ANSA METALLOCENE (ZAM) CATALYSTS FOR α-OLEFIN POLYMERIZATION

[75] Inventors: William A. Goddard, III; Christopher Brandow, both of Pasadena, Calif.

[73] Assignee: California Institute of Technology, Calif.

[21] Appl. No.: 08/907,395

[22] Filed: Aug. 7, 1997

Related U.S. Application Data
[60] Provisional application No. 60/024,395, Aug. 9, 1996.

[51] Int. Cl.$^6$ ................................................ C08F 4/44
[52] U.S. Cl. ........................ 526/134; 526/90; 526/159; 526/160; 502/117; 502/152; 556/7; 556/53
[58] Field of Search ........................ 556/7, 53; 526/90, 526/159, 160, 134; 502/152, 117

[56] References Cited

U.S. PATENT DOCUMENTS

| | | | |
|---|---|---|---|
| 5,272,236 | 12/1993 | Lai et al. | 526/348 |
| 5,278,272 | 1/1994 | Lai et al. | 526/348 |
| 5,347,024 | 9/1994 | Nickias et al. | 556/11 |
| 5,384,299 | 1/1995 | Turner et al. | 502/155 |
| 5,459,117 | 10/1995 | Ewen et al. | 502/117 |
| 5,470,993 | 11/1995 | Devore et al. | 556/11 |
| 5,486,632 | 1/1996 | Devore et al. | 556/11 |
| 5,792,819 | 8/1998 | Erker et al. | 522/134 |

OTHER PUBLICATIONS

Rufanov et al., "Hetero–ansa–metallocenes: I. Synthesis of the novel [1]–borylidene–bridged ansa–zirconocene dichloride," J. Organomet. Chem. 525 (1996) pp. 287–289.

Chang, R., Chemistry, McGraw–Hill, 1988, p. 497.

Reetz, et al., "Preparation and Catalytic Activity of Boron–Substituted Zirconocenes," *CHIMIA* vol. 49, Nr. 12, pp. 501–503 (1995).

Sun, et al., "Intramolecular Ion–Ion Interactions in Zwitterionic Metallocene Olefin Polymerization Catalysts Derived from 'Tucked–In' Catalyst Precursors and the Highly Electrophilic Boranes XB ($C_6F_5$)$_2$ (X=H, $C_6F_5$)," *J. Am. Chem. Soc.* 119:5132–43 (1997).

Rodriguez, et al., "Synthesis, Structural Characterization, and Reactivity of Zirconium Complexes Containing Trimethylenemethane–Based Ligands," *J. Am. Chem. Soc.* 119:343–52, (1997).

Kreuder, et al., "Early metal Carborane Chemistry. Generation and Reactivity of ($C_5Me_5$) ($\eta^5$–$C_2B_9H_{11}$)TiMe," *Organometallics* 14:2993–3001 (1995).

Rufanov, et al., "Hetero–ansa–metallocenes: I. Synthesis of the novel [1]–borylidene–bridged ansa–zirconocene dichloride," *J. Org. Chem.* 525:287–89 (1996).

Bochmann, et al., "Anionic and Zwitterionic Metallocene Complexes derived from Novel Boratocyclopentadienyl Ligands," *J. Chem. Soc., Chem. Commun.*, pp. 2081–82 (1995).

Woo, et al., "Combined Static and Dynamic Density Functional Study of the Ti(IV) Constrained Geometry Catalyst (CpSiH$_2$NH)TiR$^+$. 1. Resting States and Chain Propagation," *J. Am. Chem. Soc.* 118:13021–30 (1996).

Shapiro, et al., "[{$\eta^5$–$C_5Me_4$)Me$_2$Si($\eta^1$–NMe$_3$)}(PMe$_3$)–ScH]$_2$: A Unique Example of a Single–Component α–Olefin Polymerization Catalyst," *Organometallics* 9:867–69 (1990).

*Primary Examiner*—Jeffrey Smith
*Assistant Examiner*—Roberto Rabago
*Attorney, Agent, or Firm*—Limbach & Limbach LLP

[57] ABSTRACT

Single component metallocene catalysts for α-olefin polymerization are disclosed. Prior art cation metallocene catalysts have required a separate anion co-catalyst like methyl aluminoxane (MAO). However, because the inventive zwitterion ansa metallocene (ZAM) catalysts have a "built-in" anion co-catalyst functionality, the need for a separate anion co-catalyst is eliminated.

20 Claims, 2 Drawing Sheets

GROUP IV CATIONIC METALLOCENE vs. ZAM

GROUP IV ZWITTERION ANSA METALLOCENE (ZAM) CATALYSTS FOR α-OLEFIN POLYMERIZATION

CROSS REFERENCE TO RELATED APPLICATIONS

This application claims the benefit of U.S. Provisional Application No. 60/024,395 filed Aug. 9, 1996 which is incorporated herein by reference.

The U.S. Government has certain rights in this invention pursuant to Grant No. CHE-9522179 awarded by the National Science Foundation.

FIELD OF THE INVENTION

The present invention generally relates to olefin polymerization catalysts, and more specifically to single component metallocene catalysts for α-olefin polymerization.

BACKGROUND OF THE INVENTION

Polymers made by metallocene catalysts are gaining an increasing share of the worldwide plastics market. Many of these industrial catalysts are Kaminsky type ansa-metallocenes derived from 1.

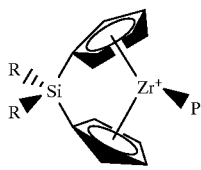

1

These catalysts require an anionic co-catalyst (or a catalyst activator), typically perfluorophenylborates or methyl aluminoxane (MAO), to generate the catalytically active cationic fourteen electron $d^0$ species.

Of the two classes of co-catalysts, MAO-based systems predominate in industrial applications. Because MAO must be present in large molar excess (200–2000 times that of the metallocene catalyst), its presence accounts for over 50% of the cost of the catalytic system. In addition to the increased expense, little is known about MAO's structure or role in the polymerization reaction. Moreover, because MAO may also provide an additional route for chain termination (via chain transfer to the trimethyl aluminum), this complicates the design of more selective catalysts.

As a result, there have been many attempts to modify the Group IV metallocene based catalytic system to eliminate the need for MAO. Although perfluorophenylborates (i.e., perfluorinated tetra-alkyl borates) may be substituted as the co-catalyst, their thermal instability and extreme sensitivity to oxygen make them impractical for large scale industrial applications.

An attractive alternative is to design a single component Ziegler Natta catalyst that does not require any co-catalyst. One such attempt is Bercaw's series of iso-electronic Group III neutral metallocenes such as 2 (Burger, et al., *Am. Chem. Soc.* 112:1566 (1990)). Although Bercaw's catalysts have been enormously useful in elucidating the basic processes involved in olefin polymerization, they are of limited use in industrial applications because of their low polymerization activity.

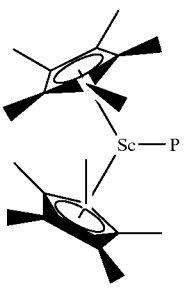

2

Another approach is to incorporate a counter anion for a Group IV catalyst directly into the ligand. In one attempt, Jordan, et al. (Crowther, et al., *J. Am. Chem. Soc.* 113:1455 (1991)) prepared catalyst in which one cyclopentadienyl (Cp) ligand is replaced by a dianionic dicarbolide ligand. As a neutral $d^0$ species, the resulting complex was expected to be capable of α-olefin polymerization. Unfortunately, these complexes readily undergo β-elimination, have low activity, and only oligomerize polypropylene. The polarization of the dicarbolide-zirconium bond is believed to result in a more neutral metal center which makes the initial binding of the propylene less exothermic and the insertion into the Zr—R bond more disfavored since the Zr orbital would be less d-like. An attempt using a trimethylene methane ligand instead of the dicarbolide ligand also produced similar results (Rodriquez G. & Bazan G. C., *J. Am. Chem. Soc.* 113:1455 (1991)).

Consequently, a need exists for a single component Ziegler-Natta catalysts that is comparable to Kaminsky type ansa-metallocenes but without the need for a co-catalyst like MAO.

SUMMARY OF THE INVENTION

Figure 1:
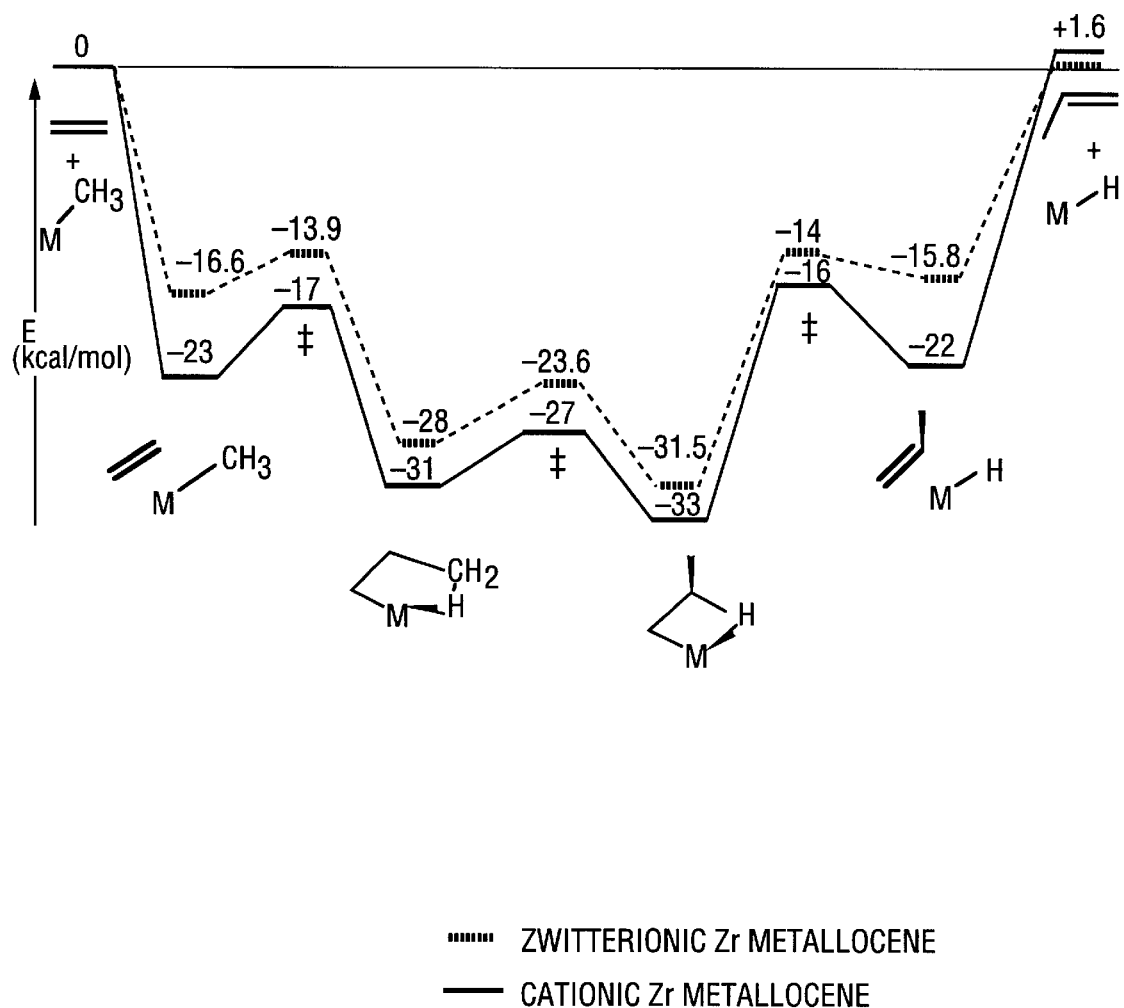
FIG. 1 illustrates the result of energy calculations comparing a zwitterion ansa metallocene (ZAM) catalyst with a standard Ziegler-Natta catalyst for each step of olefin polymerization.

A single component neutral zwitterion ansa metallocene (ZAM) catalysts are disclosed. In embodiment of the inventive catalysts, compounds are of the general formula:

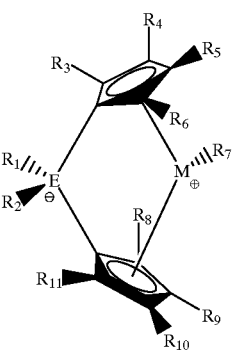

wherein

M is selected from a group consisting of Group III, Group IV, Group V, and Group VI elements;

E is boron or aluminum;

$R_1$ and $R_2$ are each independently selected from a group consisting of hydrogen, fluorine, substituted or unsubstituted $C_1$ to $C_{10}$ alkyl, substituted or unsubstituted $C_6$ to $C_{15}$ aryl, and substituted and unsubstituted $C_1$ to $C_{10}$ alkoxy;

$R_3$, $R_4$, $R_5$, $R_6$, $R_8$, $R_9$, $R_{10}$, and $R_{11}$ are each independently selected from a group consisting of hydrogen, substituted or unsubstituted $C_1$ to $C_{10}$ alkyl, substituted or unsubstituted $C_1$ to $C_{10}$ alkoxy, substituted or unsubstituted $C_6$ to $C_{15}$ aryl, substituted or unsubstituted $C_3$ to $C_{10}$ cycloalkyl, and $Si(R_{12})_3$ where $R_{12}$ is selected from the group consisting of $C_1$ to $C_{10}$ alkyl, $C_6$ to $C_{15}$ aryl, or $C_3$ to $C_{10}$ cycloalkyl; and, $R_7$ is selected from a group consisting of hydrogen, methyl, tert-butyl, benzyl, phenyl, hydride, and $Si(R_{13})_3$ where $R_{13}$ is selected from a group consisting of $C_1$ to $C_{10}$ alkyl, $C_6$ to $C_{15}$ aryl, and $C_3$ to $C_{10}$ cycloalkyl.

Moreover, each pair of adjacent radicals on the cyclopentadienyl rings (e.g., $R_4$ and $R_5$ or $R_{10}$ and $R_{11}$) together may also form a cyclic group having 4 to 15 carbon atoms which in turn may be further substituted.

Preferably, M is a Group IV metal; $R_1$ and $R_2$ are each an electron withdrawing group; and $R_3$, $R_4$, $R_5$, $R_6$, $R_8$, $R_9$, $R_{10}$, and $R_{11}$ are each selected from a group consisting of hydrogen, methyl, isopropyl, tert-butyl and trimethylsilyl. In especially preferred embodiments, M is zirconium.

The invention further includes a method for polymerizing olefins comprising the step of contacting an olefin with a catalyst of the type described above. The olefin may be a $C_3$–$C_{10}$ α-olefin, and the olefin may be contacted with the catalyst in the presence of a solvent.

DETAILED DESCRIPTION OF THE PREFERRED EMBODIMENTS

The catalysts of the present invention are zwitterion ansa metallocenes that are referred to as ZAM catalysts. The inventive catalysts eliminates the need for a counterion like MAO while retaining or improving most of the various kinetic steps in olefin polymerization over prior art Ziegler-Natta catalysts.

In one embodiment, ZAM catalysts are of the general formula:

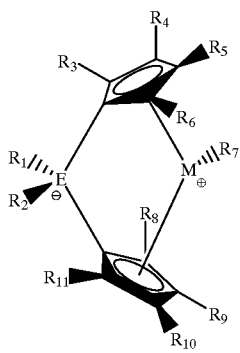

wherein

M is selected from a group consisting of Group III, Group IV, Group V, and Group VI elements;

E is boron or aluminum;

$R_1$ and $R_2$ are each independently selected from a group consisting of hydrogen, fluorine, substituted or unsubstituted $C_1$ to $C_{10}$ alkyl, substituted or unsubstituted to $C_6$ to $C_{15}$ aryl, and substituted and unsubstituted $C_1$ to $C_{10}$ alkoxy;

$R_3$, $R_4$, $R_5$, $R_6$, $R_8$, $R_9$, $R_{10}$, and $R_{11}$ are each independently selected from a group consisting of hydrogen, substituted or unsubstituted $C_1$ to $C_{10}$ alkyl, substituted or unsubstituted $C_1$ to $C_{10}$ alkoxy, substituted or unsubstituted $C_6$ to $C_{15}$ aryl, substituted or unsubstituted $C_3$ to $C_{10}$ cycloalkyl, and $Si(R_{12})_3$ where $R_{12}$ is selected from the group consisting of $C_1$ to $C_{10}$ alkyl, $C_6$ to $C_{15}$ aryl, or $C_3$ to $C_{10}$ cycloalkyl; and, $R_7$ is selected from a group consisting of hydrogen, methyl, tert-butyl, benzyl, phenyl, hydride, and $Si(R_{13})_3$ where $R_{13}$ is selected from a group consisting of $C_1$ to $C_{10}$ alkyl, $C_6$ to $C_{15}$ aryl, and $C_3$ to $C_{10}$ cycloalkyl.

Moreover, each pair of adjacent radicals on the cyclopentadienyl rings (e.g., $R_4$ and $R_5$ or $R_{10}$ and $R_{11}$) together may also form a cyclic group having 4 to 15 carbon atoms which in turn may be further substituted. Examples of compounds wherein one or more pairs of adjacent radicals form cyclic ring include but are not limited to:

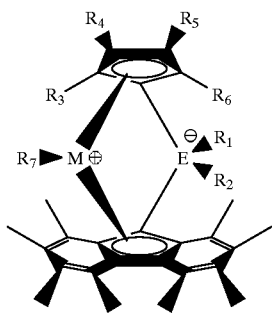

and

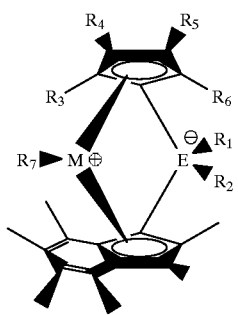

In preferred embodiments, $R_1$ and $R_2$ are each a group which increases the electrophilicity of the metal center. Illustrative examples of suitable groups include but are not limited to F, $C_6F_5$, and $CF_3$. It is also preferred that M is a Group IV metal, and $R_3$, $R_4$, $R_5$, $R_6$, $R_8$, $R_9$, $R_{10}$, and $R_{11}$ are each selected from a group consisting of hydrogen, methyl, isopropyl, tert-butyl and trimethylsilyl. In especially preferred embodiments, M is zirconium.

Another embodiment of the present invention are compounds of the general formula:

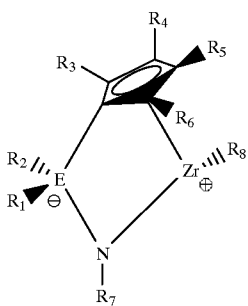

wherein

E is boron or aluminum;

$R_1$ and $R_2$ are each independently selected from a group consisting of hydrogen, fluorine, substituted or unsubstituted $C_1$ to $C_{10}$ alkyl, substituted or unsubstituted $C_6$ to $C_{15}$ aryl, and substituted and unsubstituted $C_1$ to $C_{10}$ alkoxy;

$R_3$, $R_4$, $R_5$, and $R_6$ are each independently selected from a group consisting of hydrogen, substituted or unsubstituted $C_1$ to $C_{10}$ alkyl, substituted or unsubstituted $C_1$ to $C_{10}$ alkoxy, substituted or unsubstituted $C_6$ to $C_{15}$ aryl, substituted or unsubstituted $C_3$ to $C_{10}$ cycloalkyl, and $Si(R_9)_3$ where $R_9$ is selected from the group consisting of $C_1$ to $C_{10}$ alkyl, $C_6$ to $C_{15}$ aryl, or $C_3$ to $C_{10}$ cycloalkyl, wherein each pair of adjacent radicals together also may form a substituted or unsubstituted cyclic group having 4 to 15 carbons;

$R_7$ is selected from a group consisting of hydrogen, substituted or unsubstituted $C_1$ to $C_{10}$ alkyl, substituted or unsubstituted $C_1$ to $C_{10}$ alkoxy, substituted or unsubstituted $C_6$ to $C_{15}$ aryl, substituted or unsubstituted $C_3$ to $C_{10}$ cycloalkyl, and $Si(R_{10})_3$ where $R_{10}$ is selected from the group consisting of $C_1$ to $C_{10}$ alkyl, $C_6$ to $C_{15}$ aryl, or $C_3$ to $C_{10}$ cycloalkyl; and, $R_8$ is selected from a group consisting of hydrogen, methyl, tert-butyl, benzyl, phenyl, hydride, and $Si(R_{11})_3$ where $R_{11}$ is selected from a group consisting of $C_1$ to $C_{10}$ alkyl, $C_6$ to $C_{15}$ aryl, and $C_3$ to $C_{10}$ cyclolalkyl.

In preferred compounds of this embodiment, $R_7$ is tert-butyl or trimethyl-silyl. These compounds are variations of traditional metallocene catalysts and are generally referred to as mono-Cp "constrained-geometry catalysts" (or CGC). Compounds where E=Si were one of the first single-site catalysts to be developed and are used to produce polymers which possess desirable strength properties while still allowing for easy processibility. Based upon energy calculations for single component metallocene catalysts, it is believed that these compounds would similarly display catalytic activity without the need for a co-catalyst.

The invention further includes a method for polymerizing olefins comprising the step of contacting an olefin with a catalyst of the types described above. The olefin may be a $C_3$–$C_{10}$ α-olefin, and the olefin may be contacted with the catalyst in the presence of a solvent.

The constrained-geometry embodiment of the present invention may be synthesized by known methods in the art, including but not limited to the protocol described by *Organometallics*, 9: 866–869 (1990) which is incorporated herein by reference.

The metallocene catalysts of the present invention may also be prepared by a variety of methods known in the art including the protocol described below. Although the protocol is for the preparation of $(C_6F_5)_2B(C_5H_4)_2ZrCH_3$, persons skilled in the art would readily know how to adapt the protocol for the various inventive embodiments.

$(C_6F_5)_2BCl$ is mixed with two equivalents of $Li(C_5H_4)$ $Sn(CH_3)_3$ and condensed with diethyl ether at $-78°$ C. The mixture is slowly warmed to room temperature and allowed to stir overnight. $ZrCl_4$ in toluene is slowly added and allowed to stir overnight at $80°$ C. The product is extracted from LiCl by rinsing with toluene or crashing out LiCl from the tetrahydrofuran (THF) solution with toluene, thus leaving the ligand in solution.

As illustrated by the synthetic scheme, $(C_6F_5)_2B(C_5H_4)_2ZrCH_3$ is prepared by treating $(C_6F_5)_2B(C_5H_4)_2ZrCl_2$ with two equivalents of $LiCH_3$ followed by $[B(C_6F_5)_4][C(C_6H_5)_3]$.

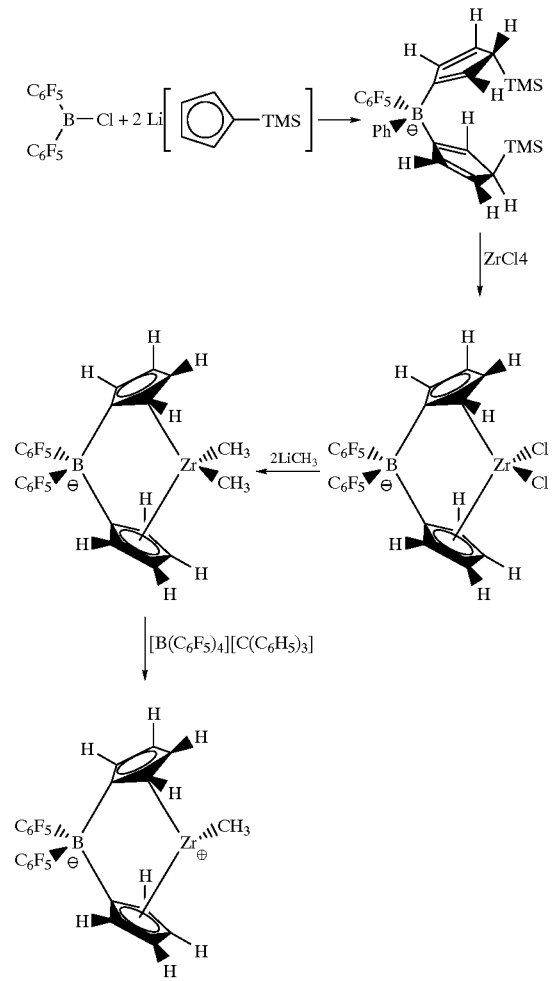

To demonstrate the performance of the inventive catalysts with prior art catalysts, the insertion reaction of methyl metallocene complexes with a molecule of ethylene was computationally followed for three illustrative ZAM catalysts and two standard Ziegler-Natt catalysts. The ZAM catalysts studied were of the formula:

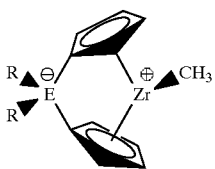

wherein R=H and E=B in embodiment I (ZAM I); R=F and E=B for embodiment II (ZAM II); and R=H and E=Al in embodiment III (ZAM III).

The two standard Group IV metallocenes were of the formula:

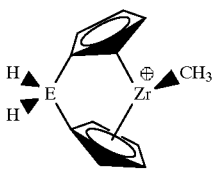

wherein E=C in control I and E=Si for control II.

Density Functional Theory (DFT) calculations were carried out using the PS-GVB-DFT program. Ringnalda, et al., PS-GVB, 2.3 Schrödinger, Inc. 1996; Slater, J. C., *Quantum Theory of Molecules and Solids*, vol, 4. *The Self-Consistent Field for Molecules and Solids* (McGraw-Hill, New York, 1974); and Perdew, J. P. *Electronic Structure Theory of Solids*, Ziesche, P. & Eschrig, H. eds. (Akademie Verlag, Berlin, 1991). The Zr was described with the LACVP Hay Wadt effective core potential (ECP) to replace the core electrons [leaving the $(4s)^2(4p)^6[(4d)(5s)(5p)]^4$ electrons to be described explicitly] and using the standard double zeta contraction. Hay, et al., *J. Phys. Chem.* 82:270 (1985). All other atoms, B, C, H, were described using the 6-31G** basis. Frisch, et al., *J. Chem. Phys.* 80:3265 (1984). Collectively this ECP Basis is referred to as LACVP**. The NLDA implementation of DFT with GGAII functional (NLDA-GGAII) as well as the Becke 3 Yang, Lee, Parr functionals (NLDA-B3LYP) were used. All geometries for stable intermediates and for transition states were fully optimized with the above basis and method. Unless otherwise noted, the geometry was optimized without geometry constraints. Interesting, despite using different ab initio methods, the energies calculated for control II are virtually identical to those previously obtained by Morokuma's group (Yoshida, et al., *Organometallics* 14:746 (1995)).

The results of the insertion reaction are summarized in FIG. 1 which displays the energies along the reaction coordinates for ZAM I and control II. As FIG. 1 illustrates, the standard cationic metallocene binds ethylene exothermically by approximately 23 kcal/mol while the corresponding ZAM binds exothermically by about 16 kcal/mol. The insertion barrier for the cationic metallocene ranges from about 6–10 kcal/mol while ZAM has an insertion barrier of just less than 3 kcal/mol. The remaining energies of the ZAM catalyst were consistent with the energies of the cationic catalyst at the same level of theory.

Figure 2:
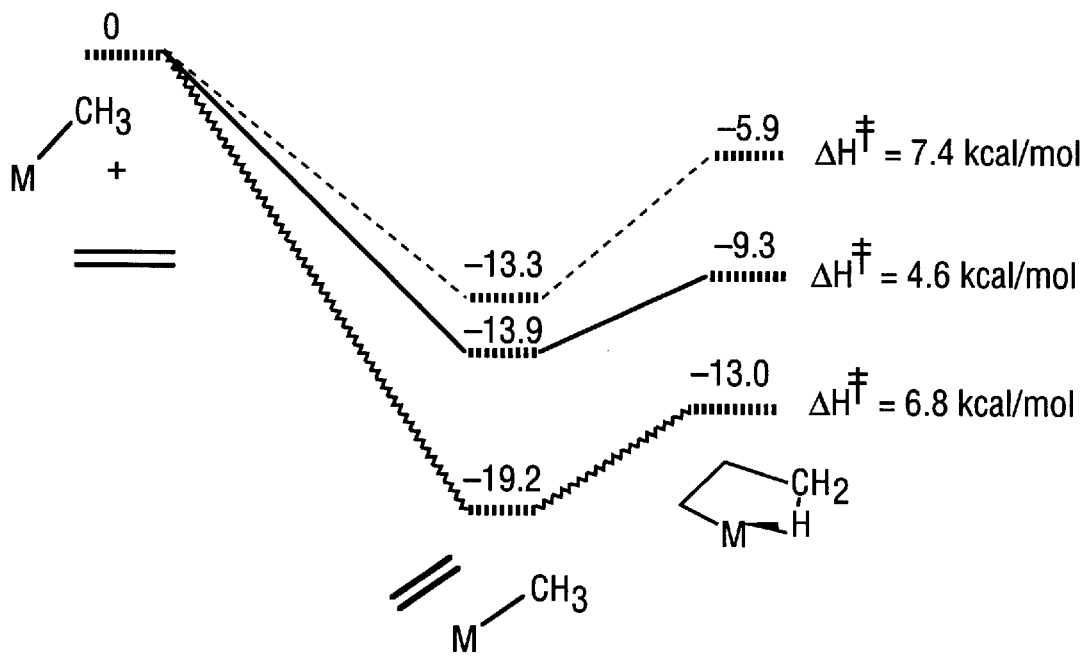
FIG. 2 illustrates transition state enthalpies for two ZAM catalysts and a standard Ziegler-Natta catalyst.

The energetics for the insertion reaction for ZAM I, ZAM III and control II are summarized in FIG. 2. The results for ZAM I and control II were calculated using DLDA-B3LYP and are consistent with the results using NLDA-GGAII.

It is to be understood that while the invention has been described above in conjunction with preferred specific embodiments, the description and examples are intended to illustrate and not limit the scope of the invention.

What is claimed is:

1. A metallocene catalyst of the formula:

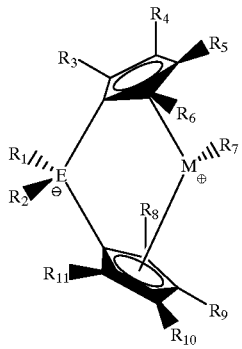

wherein

M is selected from a group consisting of Group IV, Group V, and Group VI elements;

E is boron or aluminum;

$R_1$ and $R_2$ are each independently selected from a group consisting of hydrogen, fluorine, substituted or unsubstituted $C_1$ to $C_{10}$ alkyl, substituted or unsubstituted $C_6$ to $C_{15}$ aryl, and substituted and unsubstituted $C_1$ to $C_{10}$ alkoxy;

$R_3$, $R_4$, $R_5$, $R_6$, $R_8$, $R_9$, $R_{10}$, and $R_{11}$ are each independently selected from a group consisting of hydrogen, substituted or unsubstituted $C_1$ to $C_{10}$ alkyl, substituted or unsubstituted $C_1$ to $C_{10}$ alkoxy, substituted or unsubstituted $C_6$ to $C_{15}$ aryl, substituted or unsubstituted $C_3$ to $C_{10}$ cycloalkyl, and $Si(R_{12})_3$, where $R_{12}$ is selected from the group consisting of $C_1$ to $C_{10}$ alkyl, $C_6$ to $C_{15}$ aryl, or $C_3$ to $C_{10}$ cycloalkyl, wherein each pair of adjacent radicals together also may form a substituted or unsubstituted cyclic group having 4 to 15 carbons; and, $R_7$ is selected from a group consisting of hydrogen, methyl, tert-butyl, benzyl, phenyl, hydride, and $Si(R_{13})_3$ where $R_{13}$ is selected from a group consisting of $C_1$ to $C_{10}$ alkyl, $C_6$ to $C_{15}$ aryl, and $C_3$ to $C_{10}$ cyclolalkyl.

2. The catalyst as in claim 1 wherein M is a Group IV metal.

3. The catalyst as in claim 2 wherein M is zirconium.

4. The catalyst as in claim 1 wherein E is boron.

5. The catalyst as in claim 3 wherein $R_1$, $R_2$, $R_3$, $R_4$, $R_5$, $R_6$, $R_8$, $R_9$, $R_{10}$, and $R_{11}$ are each hydrogen.

6. The catalyst in claim 3 wherein

E is boron;

$R_1$ and $R_2$ are each independently selected from a group consisting of hydrogen, fluorine, $CF_3$, and $C_6F_5$;

$R_3$, $R_4$, $R_5$, $R_6$, $R_8$, $R_9$, $R_{10}$, and $R_{11}$ are each independently selected from a group consisting of hydrogen, methyl, isopropyl, tert-butyl, and trimethylsilyl; and, $R_7$ is selected from a group consisting of methyl, tert-butyl, benzyl, phenyl, trimethylsilyl, and a hydride.

7. A metallocene of the formula comprising:

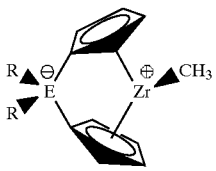

wherein
   E is boron or aluminum and
   R is selected from a group consisting of hydrogen, fluorine, substituted or unsubstituted $C_1$ $C_{10}$ alkyl, substituted or unsubstituted to $C_6$ to $C_{15}$ aryl, and substituted and unsubstituted $C_1$ to $C_{10}$ alkoxy.

8. The metallocene as in claim 7 wherein the alkyl, aryl, or alkoxy is substituted with at least one electron withdrawing group.

9. The metallocene as in claim 7 wherein the alkyl, aryl, or alkoxy is substituted with at least one fluorine atom.

10. The metallocene as in claim 9 wherein the alkyl, aryl, or alkoxy is a perfluorinated alkyl, perfluorinated aryl, or a perfluorinated alkoxy.

11. The metallocene as in claim 7 wherein E is boron.

12. The metallocene as in claim 11 wherein R is hydrogen.

13. The metallocene as in claim 11 wherein R is fluorine.

14. The metallocene as in claim 11 wherein R is $C_6F_5$ or $CF_3$.

15. A method for olefin polymerization, comprising:
   contacting the olefin with a catalyst of the formula:

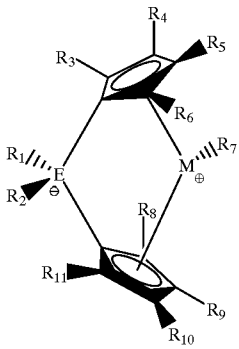

wherein
   M is selected from a group consisting of Group IV, Group V, and Group VI elements;
   E is boron or aluminum;
   $R_1$ and $R_2$ are each independently selected from a group consisting of hydrogen, fluorine, substituted or unsubstituted $C_1$ to $C_{10}$ alkyl, substituted or unsubstituted to $C_6$ to $C_{15}$ aryl, and substituted and unsubstituted $C_1$ to $C_{10}$ alkoxy;

$R_3$, $R_4$, $R_5$, $R_6$, $R_8$, $R_9$, $R_{11}$ and $R_{11}$ are each independently selected from a group consisting of hydrogen, substituted or unsubstituted $C_1$ to $C_{10}$ alkyl, substituted or unsubstituted $C_1$ to $C_{10}$ alkoxy, substituted or unsubstituted $C_6$ to $C_{15}$ aryl, substituted or unsubstituted $C_3$ to $C_{10}$ cycloalkyl, and $Si(R_{12})_3$ where $R_{12}$ is selected from the group consisting of $C_1$ to $C_{10}$ alkyl, $C_6$ to $C_{15}$ aryl, or $C_3$ to $C_{10}$ cycloalkyl, wherein each pair of adjacent radicals together also may form a substituted or unsubstituted cyclic group having 4 to 15 carbons; and,
   $R_7$ is selected from a group consisting of hydrogen, methyl, tert-butyl, benzyl, phenyl, hydride, and $Si(R_{13})_3$ where $R_{13}$ is selected from a group consisting of $C_1$ to $C_{10}$ alkyl, $C_6$ to $C_{15}$ aryl, and $C_3$ to $C_{10}$ cyclolalkyl.

16. The method as in claim 15 wherein
   M is zirconium;
   E is boron;
   $R_1$ and $R_2$ are each independently selected from a group consisting of hydrogen, fluorine, $CF_3$, and $C_6F_5$;
   $R_3$, $R_4$, $R_5$, $R_6$, $R_8$, $R_9$, $R_{10}$, and $R_{11}$ are each independently selected from a group consisting of hydrogen, methyl, isopropyl, tert-butyl, and trimethylsilyl; and,
   $R_7$ is selected from a group consisting of methyl, tert-butyl, benzyl, phenyl, trimethylsilyl, and a hydride.

17. A method for olefin polymerization, comprising:
   contacting the olefin with a catalyst of the formula:

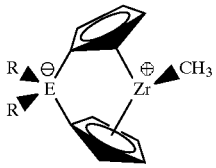

wherein
   E is boron or aluminum and
   R is selected from a group consisting of hydrogen, fluorine, substituted or unsubstituted $C_1$ to $C_{10}$ alkyl, substituted or unsubstituted $C_6$ to $C_{15}$ aryl, and substituted and unsubstituted $C_1$ to $C_{10}$ alkoxy.

18. The method as in claim 17 wherein E is boron.

19. The method as in claim 18 wherein the alkyl, aryl, or alkoxy is substituted with one or more fluorine atoms.

20. The method as in claim 18 wherein R is hydrogen, fluorine, $CF_3$, or $C_6F_5$.

* * * * *